(12) United States Patent
Hingston et al.

(10) Patent No.: US 11,779,738 B2
(45) Date of Patent: Oct. 10, 2023

(54) EXTRACELLULAR MATRIX DELIVERY DEVICE

(71) Applicant: Boston Scientific Scimed, Inc., Maple Grove, MN (US)

(72) Inventors: John A. Hingston, Framingham, MA (US); Gene T. Storbeck, Franklin, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 484 days.

(21) Appl. No.: 15/908,872

(22) Filed: Mar. 1, 2018

(65) Prior Publication Data

US 2018/0250501 A1    Sep. 6, 2018

Related U.S. Application Data

(60) Provisional application No. 62/466,182, filed on Mar. 2, 2017.

(51) Int. Cl.
| | | |
|---|---|---|
| *A61F 2/04* | (2013.01) | |
| *A61M 31/00* | (2006.01) | |
| *A61L 31/16* | (2006.01) | |
| *A61L 31/14* | (2006.01) | |
| *A61F 2/90* | (2013.01) | |
| *A61F 2/95* | (2013.01) | |
| *A61F 2/07* | (2013.01) | |

(52) U.S. Cl.
CPC ............. *A61M 31/002* (2013.01); *A61F 2/04* (2013.01); *A61F 2/90* (2013.01); *A61L 31/148* (2013.01); *A61L 31/16* (2013.01); *A61F 2/07* (2013.01); *A61F 2/95* (2013.01); *A61F 2002/045* (2013.01); *A61F 2210/0004* (2013.01); *A61F 2250/0031* (2013.01); *A61F 2250/0067* (2013.01); *A61F 2250/0068* (2013.01); *A61F 2250/0071* (2013.01)

(58) Field of Classification Search
CPC ........... A61F 2/04; A61M 31/00; A61L 31/14; A61L 31/16
See application file for complete search history.

(56) References Cited

U.S. PATENT DOCUMENTS

| | | | | |
|---|---|---|---|---|
| 2004/0098095 | A1* | 5/2004 | Burnside | A61F 2/07 623/1.13 |
| 2006/0129225 | A1* | 6/2006 | Kopia | A61B 17/115 623/1.13 |
| 2015/0231326 | A1* | 8/2015 | Milner | A61M 25/0074 604/104 |

OTHER PUBLICATIONS

B. Yue, "Biology of the Extracellular Matrix: an Overview", Journal of Glaucoma, 2014, vol. 23, No. 8, Suppl 1, S20-23, pp. 1-8.

* cited by examiner

*Primary Examiner* — Matthew W Schall
(74) *Attorney, Agent, or Firm* — Seager, Tufte & Wickhem LLP

(57) ABSTRACT

The present disclosure relates to the field of endoscopy. Specifically, the present disclosure relates to systems and methods for delivering a therapeutic agent within a body lumen, and maintaining the therapeutic agent in contact with a wall of the body lumen for a beneficial period of time. In particular, the present disclosure relates to systems and methods to prevent lesions within the gastrointestinal tract from spreading into healthy surrounding tissue.

20 Claims, 5 Drawing Sheets

EXTRACELLULAR MATRIX DELIVERY DEVICE

CROSS REFERENCE TO RELATED APPLICATIONS

The present application claims the benefit of priority under 35 U.S.C. § 119 to U.S. Provisional Patent Application Ser. No. 62/466,182, filed on Mar. 2, 2017, which is incorporated by reference in its entirety for all purposes.

FIELD

The present disclosure relates to the field of therapeutic medical devices. Specifically, the present disclosure relates to systems and methods for delivering a therapeutic agent within a body lumen, and maintaining the therapeutic agent in contact with a wall of the body lumen for a beneficial period of time. In particular, the present disclosure relates to systems and methods to aid the healing of lesions within the gastrointestinal tract.

BACKGROUND

Ulcerative colitis (UC) is a form of inflammatory bowel disease (IBD) which affects approximately 750,000 individuals in the United States. IBD impacts approximately 6 million worldwide. UC lesions often originate in or near the rectum and cause swelling, inflammation and ulceration that may extend in an uninterrupted symmetric pattern to involve all or part of the large intestine. There is no known cause for UC, although research indicates that genetics, the immune system and environmental factors are likely contributors to disease onset and clinical outcome. Current treatment strategies for UC typically focus on suppressing inflammation with aspirin-like drugs (such as 5ASA), systemic corticosteroids, immunosuppressants or biologics. Regardless of the treatment regimen, many patients become resistant to the benefits of available therapeutic agents, and require surgical intervention to remove all or a part of the colon (colectomy), which leads to challenging lifestyle changes.

Various advantageous medical outcomes may be realized by systems and methods which limit or prevent the spread of UC to the surrounding healthy tissues of the large intestine and/or allow the lumen to heal to prevent further tissue damage.

SUMMARY

The present disclosure, in its various aspects, meets an ongoing need for systems and methods for delivering and maintaining therapeutic agents within body lumens for a beneficial period of time.

In one aspect, the present disclosure relates to a medical device comprising a stent configured to move between a first configuration and a second configuration. The medical device may include at least one tube disposed about an outer wall of the stent and at least one therapeutic agent may be disposed within a lumen of the at least one tube. The medical device may further include a covering disposed on an inner wall or an outer wall of the stent. A portion of the least one tube may include a planar surface that may contact the outer wall of the stent. The at least one tube may include an oblong cross-section. The at least one therapeutic agent may include a liquid, gel or a powder. A diameter of the medical device in the first configuration may be about 30-50% of a diameter of the medical device in the second configuration. The at least one tube may include a plurality of tubes configured such that an outer surface of adjacent tubes may contact each other when in the second configuration. The at least one tube may include a plurality of tubes configured such that an outer surface of adjacent tubes may not contact each other when in the first configuration. The at least one tube may include a biodegradable or bioabsorbable material. In addition, or alternatively, the at least one tube may include a permeable or semi-permeable material. In addition, or alternatively, the at least one tube may be configured to rupture along one or more portions of the tube when the stent is in the second configuration.

In another aspect, the present disclosure relates to a medical device comprising a stent configured to move between a first configuration and a second configuration. The medical device may include at least one tube disposed on an outer wall of the stent, wherein a lumen of the at least one tube may be configured to be at least partially filled with a therapeutic agent. The medical device may include a covering disposed on an inner wall or an outer wall of the stent. The at least one therapeutic agent may include a liquid, gel or a powder. The at least one tube may include a biodegradable or bioabsorbable material. In addition, or alternatively, the at least one tube may include a permeable or semi-permeable material. In addition, or alternatively, the at least one tube may be configured to rupture along one or more portions of the tube when the stent is in the second configuration.

In another aspect, the present disclosure relates to a method comprising positioning a medical device within a body lumen. The medical device may comprise a stent, at least one tube may be disposed about an outer wall of the stent, and at least one therapeutic agent may be disposed within a portion of the at least one tube. The method may further include moving the stent from a first configuration to a second configuration such that at least a portion of the at least one tube may contact an inner wall of the body lumen. The method may further include releasing at least a portion of the therapeutic agent from the at least one tube into contact with at least a portion of the inner wall of the body lumen. The method may further include contacting at least a portion of the therapeutic agent with a lesion on or within the inner wall of the body lumen.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

Figure 1A:
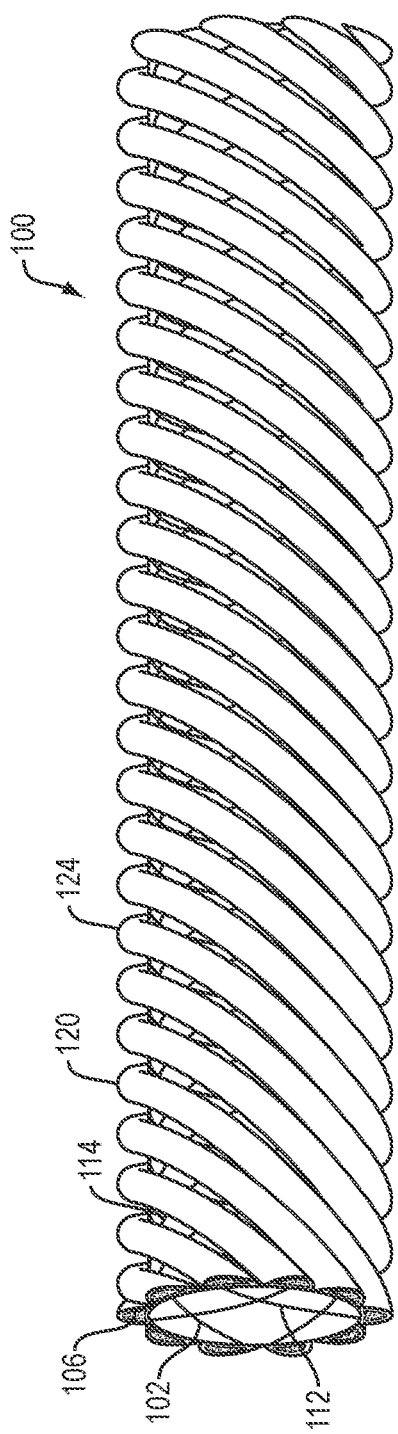
FIG. 1A provides a schematic view of a medical device in a non-expanded configuration, according to an embodiment of the present disclosure.

It is noted that the drawings are intended to depict only typical or exemplary embodiments of the disclosure. It is further noted that the drawings may not be necessarily to scale. Accordingly, the drawings should not be considered as limiting the scope of the disclosure. The disclosure will now be described in greater detail with reference to the accompanying drawings.

DETAILED DESCRIPTION

The present disclosure is not limited to the particular embodiments described. The terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to the treatment of the lower gastrointestinal (GI) tract, it should be appreciated that such systems and methods may be used in a variety of bodily organs and/or lumens to address a variety of medical conditions where delivery of a therapeutic agent is beneficial, including for example, the stomach, esophagus, large intestine, small intestine, rectum, urinary system, respiratory system, reproductive system and/or circulatory system.

As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, steps, elements and/or components, but do not preclude the presence or addition of one or more other features, regions, integers, steps, operations, elements, components, and/or groups thereof.

As used herein, the term "distal" refers to the end farthest away from a medical professional when introducing a device into a patient, while the term "proximal" refers to the end closest to the medical professional when introducing a device into a patient.

As used herein, the term "expanded" refers to an increase in size, diameter or profile as compared to the size, diameter or profile in an "unexpanded," "non-expanded" or "collapsed" configuration.

As used herein, extracellular matrix (ECM) refers to a multi-domain network of macromolecules organized in a cell/tissue-specific manner. Major components of the ECM include collagens, proteoglycans, elastins and cell-binding glycoproteins which contribute to the mechanical properties of tissues and provide a reservoir of growth factors and other bioactive molecules with tissue regenerative properties. In various embodiments of the present disclosure, ECM may be provided in the form of liquids, powders and/or or gels.

The present disclosure relates generally to systems and methods for delivering a therapeutic agent, e.g., treating lesions within the GI tract with an expandable/collapsible (e.g., non-expandable) medical device configured to deliver and maintain a therapeutic agent in contact with the affected region of the GI tract tissue wall. Although the present disclosure provides specific reference to delivery of ECM within the GI tract, in various embodiments, the systems and methods disclosed herein may beneficially deliver a variety of therapeutic agents within a variety of body lumens or organs for a variety of local (e.g., lesions, ulcers, inflammations, etc.) or systemic ailments, medical conditions and the like.

Figure 1B:
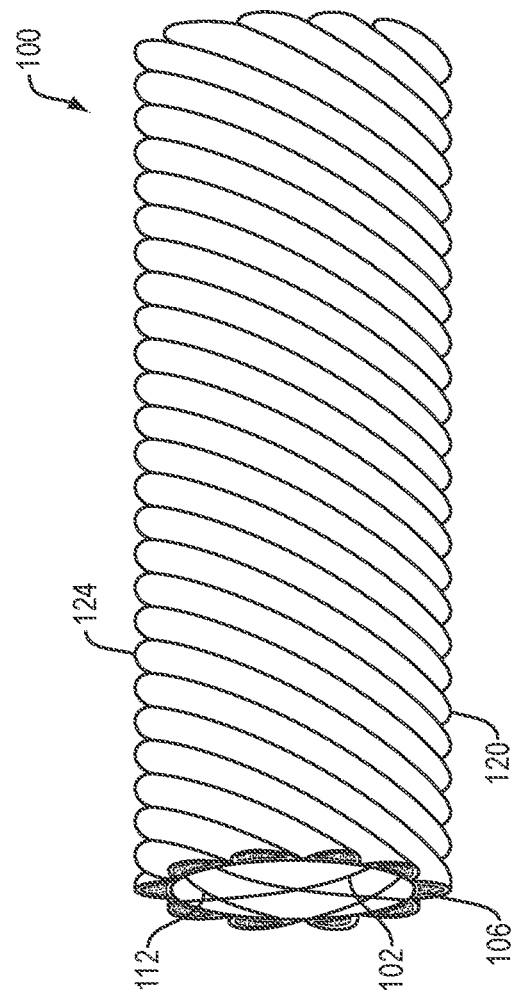
FIG. 1B provides a schematic view of a medical device in an expanded configuration, according to an embodiment of the present disclosure.
Figure 1D:
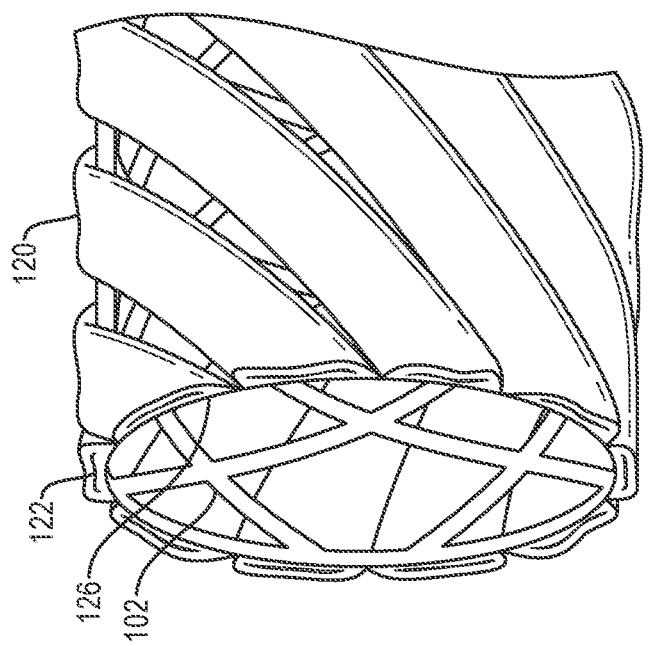
FIG. 1D provides a schematic view of an unloaded medical device, in accordance with an embodiment of the present disclosure.
Figure 1C:
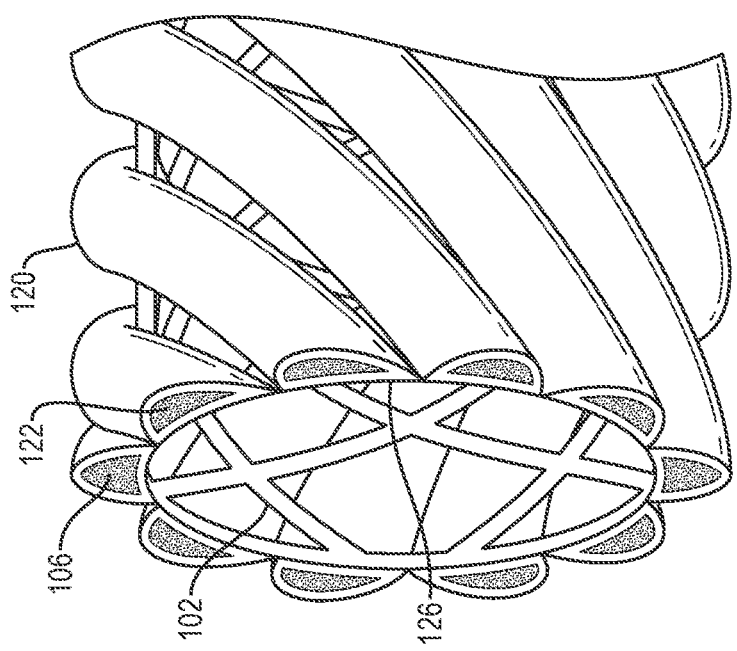
FIG. 1C provides a schematic view of a medical device loaded with a therapeutic agent, according to an embodiment of the present disclosure.

Referring to FIGS. 1A-1B, in one embodiment, the present disclosure provides a medical device 100 that includes a stent 102 configured to move between a first (e.g., non-expanded or compressed) configuration and a second (e.g., expanded) configuration. For example, a length of the stent may decrease by up to approximately 50 percent as it moves from the first configuration to the second configuration, and a diameter of the stent may increase by up to approximately 50 percent as the stent moves from the first configuration to the second configuration, including any percent range of decrease or increase up to 50 percent. The stent may include a variety of woven, braided or interlaced materials (e.g., metals, polymeric materials, biodegradable materials, etc.) which define an inner wall 112 and an outer wall 114. Although the stents disclosed herein are generally depicted as including woven or braided materials, in various embodiments, the stents may include laser cut stents which may or may not change in length (e.g., shorten) as the stent moves from the first configuration to the second configuration. The stents in various configurations may be self-expanding or expandable such as balloon-expandable. A covering may be disposed along the inner and/or outer wall 112, 114 to fully or partially enclose the weave of the stent 102. One or more tubes 120 may be disposed about the outer wall 114 of the stent 102 in a variety of patterns or configurations. Although FIG. 1A depicts ten tubes 120 disposed in a helical pattern about the outer wall 114 along the length of the stent, any number of tubes may be disposed in a variety of different patterns, configurations, densities or orientations about the inner or outer wall of the stent. With the stent 102 in the first configuration (FIG. 1A), the tubes 120 may be spaced apart along the outer wall 114 of the stent 102 such that the outer surface 124 of adjacent tubes 120 do not contact each other, and the underlying stent 102 is partially visible. As the stent 102 moves to the second configuration (FIG. 1B), the length of the stent decreases and the diameter of the stent increases such that a portion of the outer surface 124 of adjacent tubes 120 are placed in direct contact with each other, thereby hiding or covering the underlying stent 102. The tubes 120 may be formed from a suitably compliant material to allow each tube to expand as the stent moves from the non-expanded to expanded configuration. Referring to FIG. 1C, in one embodiment, the tubes 120 may include a hemispherical shape in which a planar surface 126 of the tubes 120 lay substantially flat along the length of the outer wall 114 of the stent 102. In various embodiments, a cross-section of the one or more tubes may vary in shape and may include, by way of non-limiting example, oblong, elliptical and/or triangular shapes.

In one embodiment, the one or more tubes 120 may be adhered or affixed along the full length of the outer wall 114 of the stent 102 using a suitable glue, resin or adhesive. Alternatively, one or both ends of each tube 120 may be attached to the outer wall 114 at the respective ends of the stent, thereby leaving a portion or portions, such as a middle portion, of each tube 120 unattached (e.g., floating) along the length of the stent. As the stent 102 moves from the non-expanded to expanded configuration, the tubes 120 may be firmly secured to the outer wall 114 of the stent as the diameter of the stent increases. In another embodiment, each tube may be adhered or affixed at even or uneven intervals along the outer wall 114 of the stent 102.

Referring to FIG. 1C, each tube 120 may define a lumen 122 which is loaded or filled with a therapeutic agent 106 (e.g., ECM) in the form of, e.g., a liquid, gel or a powder. In various embodiments, the therapeutic agent is not limited to ECM, but may include a variety of agents or materials both alone or in combination, including anti-inflammatory agents, anti-proliferative agents, pain medications, and the like. Alternatively, referring to FIG. 1D, the stent 102 may be provided with one or more empty tubes 120 disposed along the length of the outer wall 114. The tubes 120 may be filled with a desired therapeutic agent (e.g., using a syringe) immediately prior to the medical procedure. The ability to provide the tubes 120 in an empty or unloaded configuration may be beneficial in situations in which the therapeutic agent has a short shelf life, and cannot be maintained within the tubes for a prolonged period of time, e.g., during shipment and storage.

The one or more tubes 120 may include a variety of different designs, materials, thicknesses, layers, configurations and/or compositions to effect release of the therapeutic agent 106 contained therein. In one embodiment, the one or more tubes 120 may comprise a biodegradable or bioabsorbable material (e.g., polylactic acid, polylactic-co-glycolic acid, polydioxanone polyadipate butyrate, polyadipate butyrate terephthalate, etc.) which dissolves or degrades over some period of time upon contact with a tissue wall of a body lumen to release the therapeutic agent. The thickness and/or composition of the one or more tubes may be varied to deliver the therapeutic agent 106 across a variety of time intervals (e.g., fast or slow release of the therapeutic agent) depending on the patient's clinical requirements. For example, a portion of the one or more tubes 120 disposed along the outer wall 114 of the stent 102 may be configured to dissolve within, e.g., 5-10 minutes for rapid release of the therapeutic agent, while other of the one or more tubes 120 may be configured for slower release of the therapeutic agent 106. For example, the one or more tubes 120 may be configured to release a therapeutic agent in the form of a liquid or gel within minutes to hours after the stent is placed within a body lumen. Alternatively, the one or more tubes 120 may be configured to deliver a therapeutic agent in the form of a powder within days, weeks or months after the stent is placed within a body lumen. In various embodiments, a portion of the tubes may be loaded with a therapeutic agent in the form of a liquid or gel for short-term release within the body lumen, and another portion of the tubes or other of the tubes may be loaded with a therapeutic agent in the form of a powder for long-term release within the body lumen. In addition, or alternatively, individual tubes 120 may be loaded with different forms and/or concentrations of therapeutic agent for delivery across a variety of time intervals. In another embodiment, the one or more tubes 120 may comprise a permeable or semi-permeable material (e.g., porous membrane, etc.) through which the therapeutic agent may pass or diffuse without the tube substantially degrading. As above, the thickness, composition and/or pore size of the one or more tubes 120 may be varied to effect slower or faster release of the therapeutic agent 106. In yet another embodiment, the one or more tubes 120 may comprise a material configured to rupture or burst when the stent moves to the second configuration. For example, one or more of the tubes 120 may include a wall thickness configured to rupture when stretched beyond a threshold level. The ruptured tubes 120 may therefore provide an immediate burst of therapeutic agent onto the tissue wall of the body lumen. In various embodiments, the stent 102 may include any combination of these or other tube configurations according to the type, size, location and/or severity of the lesion(s) in need of treatment.

Figure 2A:
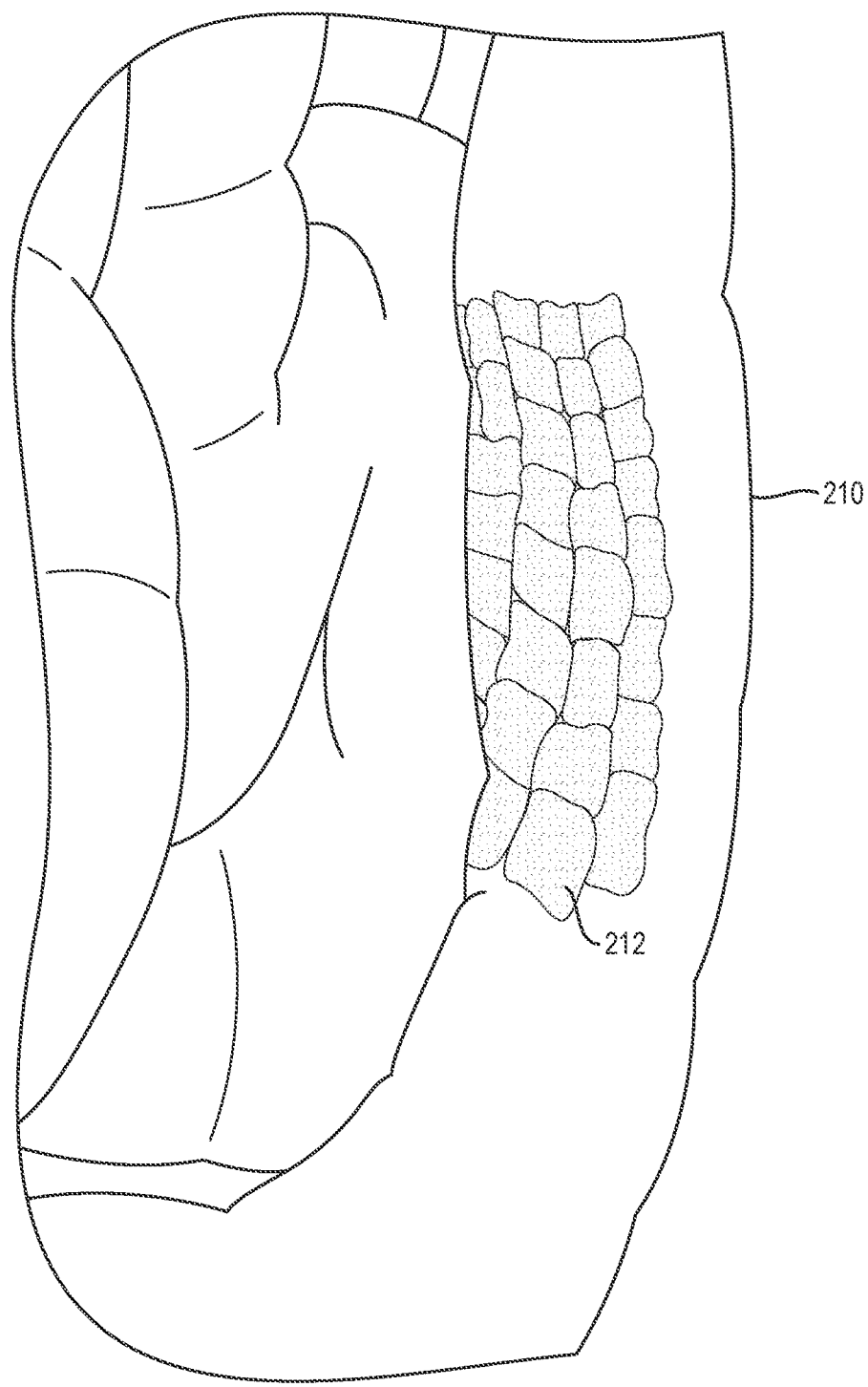
FIG. 2A illustrates a body lumen that includes a lesion, in accordance with an embodiment of the present disclosure.

As illustrated in FIG. 2A, a lesion 212 of the colon 210 may manifest as an inflamed reddish region with a cobblestone-like appearance. These lesions typically form in small localized regions as the outer epithelial layer breaks down, and tend to spread as the contents of the colon contact and further irritate and degrade the surrounding healthy epithelial layer. Accordingly, a medical device 100 of the present disclosure may find advantageous use when deployed within the colon before the lesions spread into the healthy surrounding tissues.

Figure 2B:
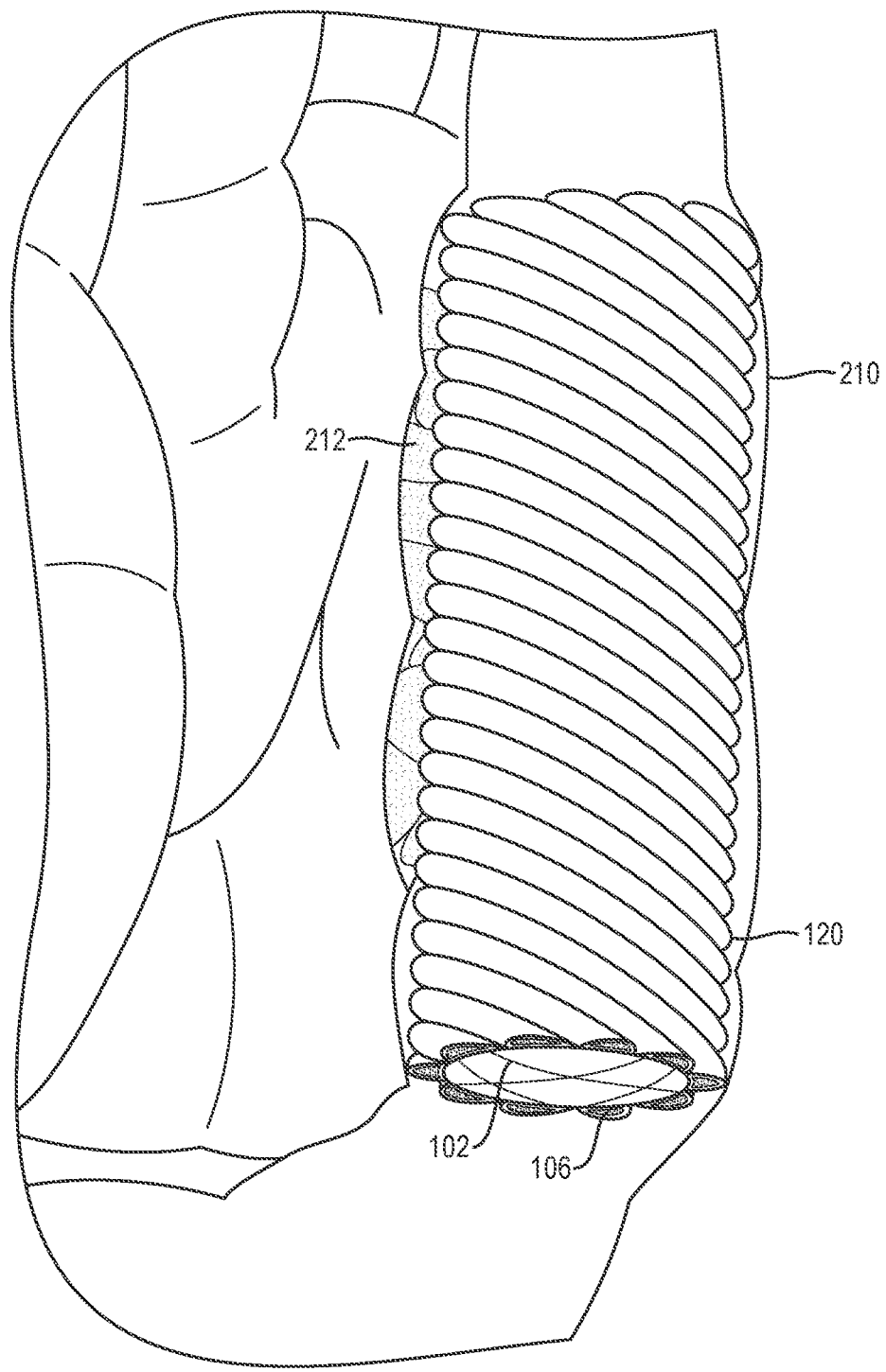
FIGS. 2B-2C provide schematic views of a medical device disposed within a body lumen that includes a lesion, in accordance with an embodiment of the present disclosure.

Referring to FIG. 2B, a stent 102 of the present disclosure may be advanced into the colon in the first configuration. Once properly positioned, the stent 102 may be moved to the second configuration such that the outer surface of one or more of the tubes 120 are placed in direct contact with the wall of the colon 210 and the lesion 212. The stent 102 may be configured, in the second configuration, to apply a sufficiently low radial force to maintain the stent in the proper location without stretching or otherwise distending the colon and/or further irritating the lesion. For example, the stent 102 may apply approximately 50% or less of the radial force of a conventional colonic stent. In addition, or alternatively, the outer wall 114 of the stent 102 and/or the outer surface 124 of the tube(s) 120 may include a one or more attachment elements (e.g., barbs, hooks, fingers, etc.) configured to atraumatically engage the wall of the body lumen (e.g., colon, etc.) to prevent or minimize migration of the stent disposed therein.

Figure 2C:
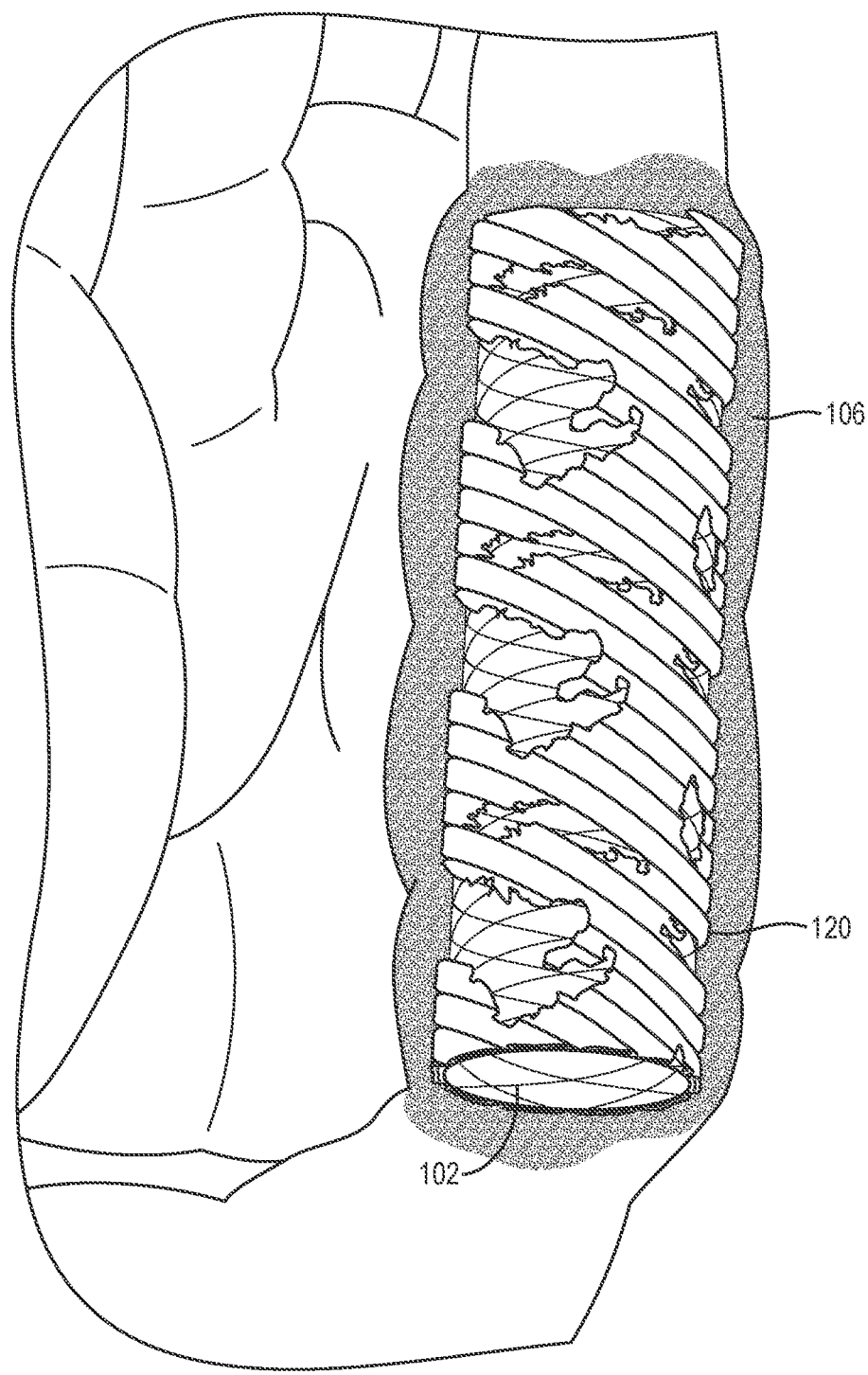

Referring to FIG. 2C, the therapeutic agent 106 may be released into the space between the stent 102 and the wall of the colon 210 as the one or more tubes 120 deflate, dissolve and/or degrade. The partially deflated, degraded or dissolved tubes 120 may provide the additional benefit of preventing the therapeutic agent 106 from passing through the woven braid of the stent 102, thereby maintaining the therapeutic agent in contact with the lesion 212. Additionally, the partially dissolved tubes 120 may block or shield the contents of the colon 210 flowing through the lumen 122 of the stent 102 from contacting and further irritating the lesion 212. As discussed above, a covering disposed along the inner and/or outer wall 112, 114 of the stent 102 may further prevent the contents of the colon from contacting the lesion 212, and also maintain the therapeutic agent between the stent and wall of the colon.

Although FIGS. 2B and 2C depict the placement of a single stent 102 over a single lesion 212 within the colon, in various embodiments any number of stents may be placed throughout the GI tract depending on the size and/or number of lesions. The stent 102 may be biodegradable and/or pass from the patient during the body's natural course. Alternatively, the stent may be non-biodegradable and is removed and/or replaced by a medical professional, e.g., during a routinely scheduled colonoscopy.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
   a stent configured to move between a first configuration and a second configuration;
   a plurality of tubes disposed about an outer wall of the stent in a helical pattern, wherein the plurality of tubes are biodegradable or bioabsorbable; and
   at least one therapeutic agent disposed within lumens of the plurality of tubes.

2. The medical device of claim 1, further comprising a covering disposed on an inner wall or the outer wall of the stent.

3. The medical device of claim 1, wherein a portion of the plurality of tubes includes a planar surface that contacts the outer wall of the stent.

4. The medical device of claim 1, wherein the plurality of tubes include an oblong cross-section.

5. The medical device of claim 1, wherein the at least one therapeutic agent comprises a liquid, gel or a powder.

6. The medical device of claim 1, wherein a diameter of the medical device in the first configuration is about 30-50% of a diameter of the medical device in the second configuration.

7. The medical device of claim 1, wherein outer surfaces of adjacent tubes contact each other when in the second configuration.

8. The medical device of claim 1, wherein outer surfaces of adjacent tubes do not contact each other when in the first configuration.

9. The medical device of claim 1, wherein the plurality of tubes comprise a biodegradable or bioabsorbable material.

10. The medical device of claim 1, wherein the plurality of tubes comprise a permeable or semi-permeable material.

11. The medical device of claim 1, wherein the plurality of tubes are configured to rupture along one or more portions of the plurality of tubes when the stent is in the second configuration.

12. A medical device comprising:
    a stent configured to move between a first configuration and a second configuration; and
    a plurality of tubes disposed in a helical pattern on an outer wall of the stent, wherein lumens of the plurality of tubes are configured to be at least partially filled with a therapeutic agent, and wherein the plurality of tubes are biodegradable or bioabsorbable.

13. The medical device of claim 12, further comprising a covering disposed on an inner wall or the outer wall of the stent.

14. The medical device of claim 12, wherein the therapeutic agent comprises a liquid, gel or a powder.

15. The medical device of claim 12, wherein the plurality of tubes comprise permeable or semi-permeable material.

16. The medical device of claim 12, wherein the plurality of tubes are configured to rupture along one or more portions of the tube when the stent is in the second configuration.

17. A medical device, comprising:
    a stent configured to move between a first configuration having a first diameter and a second configuration having a second diameter greater than the first diameter;
    a plurality of tubes disposed about an outer wall of the stent in a helical pattern, wherein adjacent tubes comprise outer surfaces which do not contact each other when in the first configuration and which contact each other when in the second configuration; and
    at least one therapeutic agent disposed within lumens of the plurality of tubes.

18. The medical device of claim 17, wherein the plurality of tubes are biodegradable or bioabsorbable.

19. The medical device of claim 17, wherein the first diameter is about 30-50% of the second diameter.

20. The medical device of claim 17, wherein the plurality of tubes comprises a permeable or semi-permeable material.

* * * * *